United States Patent [19]
Thoms

[11] 3,992,928
[45] Nov. 23, 1976

[54] MEASURING THE STRENGTH OF A ROCK FORMATION IN SITU

[76] Inventor: Robert L. Thoms, 7625 N. Coventry Circle, Baton Rouge, La. 70808

[22] Filed: Nov. 28, 1975

[21] Appl. No.: 635,807

[52] U.S. Cl. .............................................. 73/88 E
[51] Int. Cl.² ............................................ G01N 3/10
[58] Field of Search .................. 73/88 E, 88 C, 151

[56] References Cited
UNITED STATES PATENTS
3,457,778  7/1969  Gill et al. ........................... 73/88 E Primary Examiner—James J. Gill
Assistant Examiner—Anthony V. Ciarlante
Attorney, Agent, or Firm—George F. Helfrich

[57] ABSTRACT

Two hollow cylinders of rock are formed in the rock formation to be tested. A pressure ring is applied to the interior of one of the hollow cylinders of rock, and the ring is pressurized until the cylinder fractures, the highest value of the pressure being recorded as a measure of the tensile strength of the rock. A pressure ring is applied to the exterior of the other hollow cylinder of rock, and the ring is pressurized until the cylinder fractures, the highest value of the pressure being recorded as a measure of the compression strength of the rock.

5 Claims, 5 Drawing Figures

MEASURING THE STRENGTH OF A ROCK FORMATION IN SITU

BACKGROUND OF THE INVENTION

1. Field of the Invention

This invention relates generally to measuring and testing. More particularly, the invention relates to the tensile and compression strength testing of a rock formation — esp., an underground rock formation — in situ.

2. Prior Art

Caverns in rock formations — e.g., solution caverns in salt domes or bedded salt — are being used increasingly for the storage of petroleum products (e.g., natural gas) and other important fluids under pressure. As a consequence, the surrounding rock formations are loaded by both tensile and compressive stresses. Upon the pressurization of the caverns, fissures in the surrounding rock formations sometimes occur, with resulting losses of valuable fluid products.

An urgent need therefore exists for a non-destructive method which would afford the effective, rapid, and economical measurement of the tensile and compression strengths of rock formations — esp. underground rock formations — thereby providing a positive determination of the suitability of such rock formations for the storage of fluids under pressure.

Accordingly, a number of attempts have been made by prior inventors to provide such a method. As an example, Hardy and Jayaraman have proposed a method in the *Society of Petroleum Engineers Journal*, June, 1972, at p. 246. Howsoever efficacious, this method is found wanting, in that samples of rock must be removed from the formation in question and taken to the laboratory for testing, thereby consuming valuable time. A number of other proposed methods of the prior art also suffer from this disadvantage. Additional methods and devices of note are found in the following U.S. Pat. Nos. 3,796,091 (Serata); 3,446,062 (Goodman); 3,364,737 (Comes); and 2,957,341 (Menard). However, none provides the desired combination of non-destructivity, rapidity, economy, and efficiency in the measurement of tensile and compression strengths of rock (as distinguished from the measurement of stress, modulus, etc.).

SUMMARY OF THE INVENTION

It is therefore the primary object of the present invention to provide a method for measuring the tensile strength and the compression strength of a rock formation, which method obviates the inadequacies of the prior art and presents a significant advance in the technology of measuring and testing. This object is achieved by the provision of a process which comprises:

a. cutting two concentric annular cavities in the rock formation to form a hollow cylinder of rock which remains connected to the rock formation at one end and is supported thereby;

b. inserting into the inner annular cavity a cylindrical support having an expandable collar, most advantageously a narrow one, secured to its outer surface and positioned perpendicularly to its longitudinal axis, the expandable collar communicating with means for the supply thereto of a fluid under pressure;

c. applying end pressure to the hollow cylinder of rock and pressurizing the expandable collar with fluid so that the collar expands against the hollow cylinder of rock surrounding it and causes the hollow cylinder of rock to fracture;

d. monitoring the fluid pressure as the collar is pressurized and the hollow cylinder of rock is caused to fracture, and recording the highest value of the pressure as a measure of the tensile strength of the rock;

e. cutting a second pair of concentric annular cavities in the rock formation to form a second hollow cylinder of rock which remains connected to the rock formation at one end and is supported thereby;

f. inserting into the outer of the second pair of concentric annular cavities a hollow cylindrical support having an expandable collar, most advantageously a narrow one, secured to its inner surface and positioned perpendicularly to its longitudinal axis, the expandable collar communicating with means for the supply thereto of a fluid under pressure;

g. applying end pressure to the second hollow cylinder of rock and pressurizing the expandable collar with fluid so that the collar expands against the second hollow cylinder of rock which it surrounds and causes the second hollow cylinder of rock to fracture; and h. monitoring the fluid pressure as the expandable collar is pressurized and the second hollow cylinder of rock is caused to fracture, and recording the highest value of the pressure as a measure of the compression strength of the rock.

If desired for any reason, tensile strength alone may be determined, as by following steps (a) – (d) above; similarly, compression strength alone may be determined, as by following steps (e) – (h) above.

In the practice of the present invention, when the rock formation to be tested is an underground rock formation, very beneficial results are obtained if the hollow cylinders of rock are cut in the formation at the base of a bore hole, which may be vertical, inclined from the vertical, or even horizontal if required or desired for any reason.

Moreover, it is preferred to employ an inflatable membrane as the expandable collar for one or both of the cylindrical supports which are inserted into the annular cavities.

BRIEF DESCRIPTION OF THE DRAWING

For a more complete understanding of the present invention, including its primary object and benefits, reference should be made to the description of the preferred embodiments, which is set forth in detail below. This description should be read together with the accompanying drawing, wherein.

DESCRIPTION OF THE PREFERRED EMBODIMENTS

Figure 1:
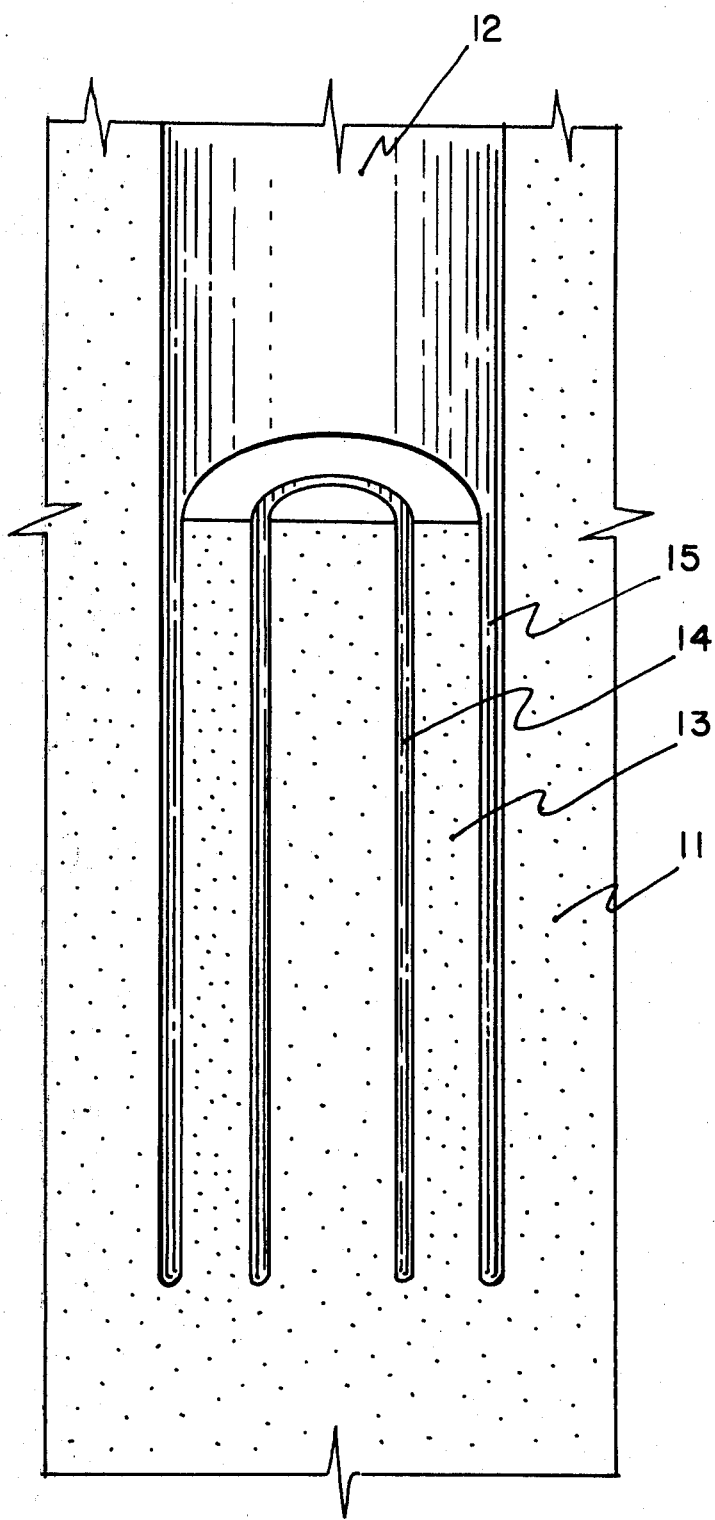
FIG. 1 is a schematic, cut-away illustration showing a bore hole, at the base of which two concentric annular cavities have been cut in order to form a hollow cylinder of rock in the rock formation to be tested.

Although of equal utility in respect of both above- and underground rock formations, the method of the present invention is particularly advantageously employed in the testing of underground rock formations. FIG. 1 shows such a rock formation 11 at the base of bore hole 12, which has been drilled according to standard methods, employing drilling devices well known to those of skill in the art and readily available commercially. Although shown in the drawing to be vertical, bore hole 12 may be also inclined from the vertical, or even horizontal, depending upon the location of the underground rock formation and other factors immediately apparent to those of skill in the art. Of course, a bore hole may not be necessary in the testing of rock formations which are found but a short distance from the surface of the earth. As pictured in FIG. 1, hollow rock cylinder 13 is cut in rock formation 11, and remains connected at its lower end to the formation and is supported thereby. This is accomplished by cutting two concentric annular cavities — inner annular cavity 14 and outer annular cavity 15 — in rock formation 11 at the base of bore hole 12 by means of a dual — barrel, diamond coring drill, which is known in the art (see, e.g., Hardy and Jayaraman, supra). Inner annular cavity 14, which is shown in the drawing to be tubular, may be cylindrical in configuration, if desired for any reason. Either alternative will result in the production of a hollow cylinder of rock 13 which is suitable in the practice of the instant process.

Figure 2:
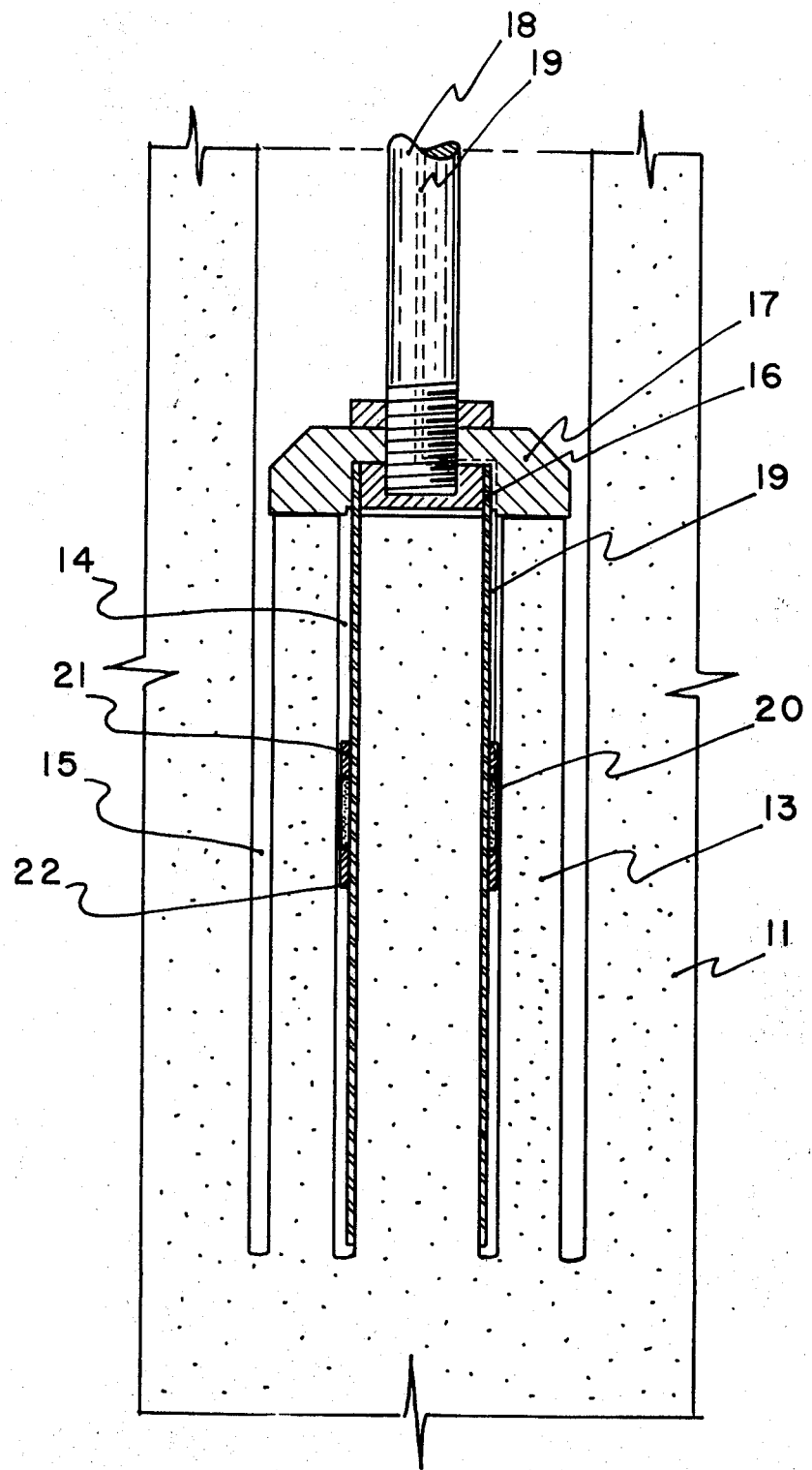
FIG. 2 is a partial sectional view of a means for (*a*) applying end pressure to the hollow cylinder of rock of FIG. 1, and (*b*) applying a pressure ring to the interior of the hollow cylinder of rock of FIG. 1.
Figure 3:
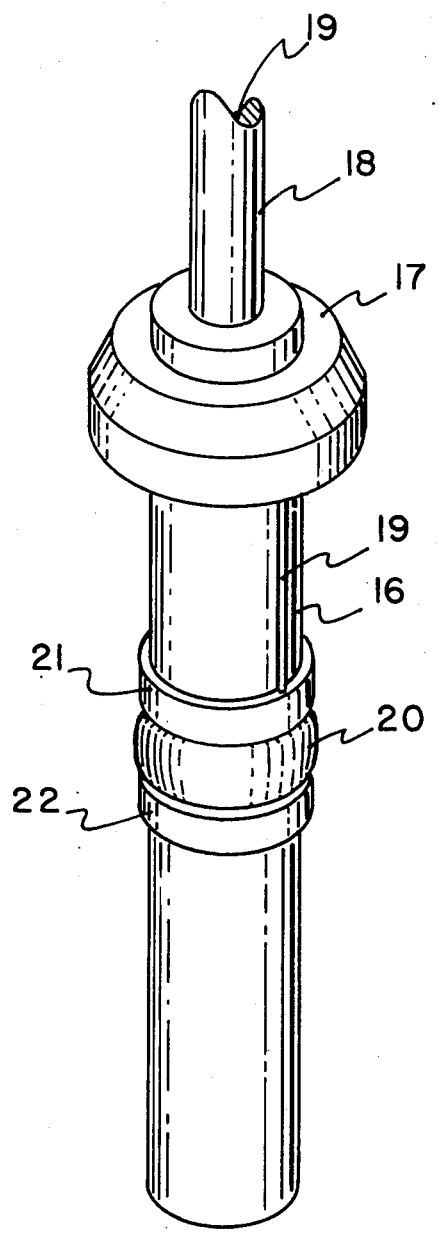
FIG. 3 is a perspective view of the means pictured in FIG. 2.

Inserted into inner annular cavity 14 is cylindrical support 16, to which, end pressure loading head 17 is fixedly attached, as shown in FIG. 2. Insertion is facilitated by means of stem 18, which is secured to end pressure loading head 17, and through which fluid pressure line 19 passes. Fluid pressure line 19 communicates with expandable collar 20 and a source of fluid — esp. a gas — under pressure (not shown), and standard means for measuring — and preferably recording — the value of the pressure of the fluid (not shown). If inner annular cavity 14 is cylindrical instead of tubular, cylindrical support 16 need not be hollow as is shown in FIG. 2. Expandable collar 20, which is advantageously an inflatable membrane fabricated from any of a number of commercially — available polymeric sheets or films of superior tensile strength, elongatability and elasticity — e.g., chlorinated polyethylene — is secured to the outer surface of cylindrical support 16 in a position perpendicular to the longitudinal axis of cylindrical support 16, and is partially confined by barrier rings 21 and 22, which give direction to the subsequent expansion of expandable collar 20. As is shown in the drawing, expandable collar 20 is advantageously a narrow band, because of the facility in both the construction and manipulation thereof, in view of its efficacy, which is unexpected. FIG. 3 shows cylindrical support 16 and its attachments in perspective, in order that the construction and utilization thereof might be better understood.

After insertion of cylindrical support 16 into inner annular cavity 14, end pressure is applied to hollow rock cylinder 13 by end pressure loading head 17 through stem 18. Moreover, expandable collar 20 is pressurized with fluid so that it expands against hollow rock cylinder 13 until a fracture thereof occurs, the fluid pressure being monitored throughout this procedure. Upon fracture of hollow rock cylinder 13, the fluid pressure drops momentarily. Accordingly, the highest value of the monitored fluid pressure is recorded as a measure of the tensile strength of rock formation 11. As is immediately apparent to those of skill in the art, a prior calibration of the instant method will afford an immediate determination of the tensile strength of rock formation 11.

Figure 4:
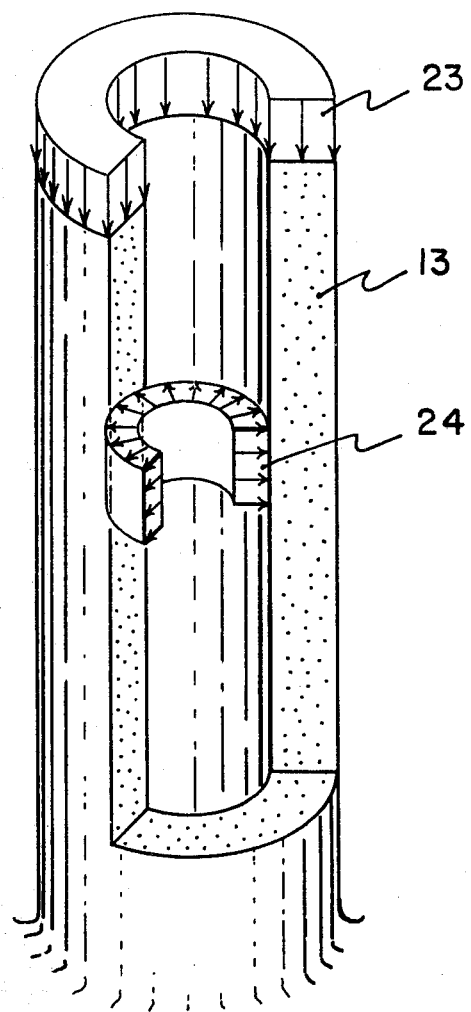
FIG. 4 schematically illustrates the principle of operation of that section of the instant process which relates to the measurement of the tensile strength of the rock formation, the procedural steps of which are understood with reference to FIGS. 1–3.

FIG. 4 schematically depicts the two loading arrangements that are applied to hollow rock cylinder 13 in the first section of the process of the present invention: viz., end pressure 23, and the pressure 24 resulting from expansion of the expandable collar.

It should be pointed out that the procedural steps in this section of the instant process — as well as those of the second section, which is described below — are ordinarily accomplished sequentially. However, certain of the individual steps may be accomplished virtually simultaneously, without any departure from the spirit and scope of the invention as presently comprehended. By way of example, cutting of the concentric annular cavities and insertion of the cylindrical support may be substantially simultaneously accomplished when the cylindrical support comprises coring means communicating with the lower end thereof.

Figure 5:
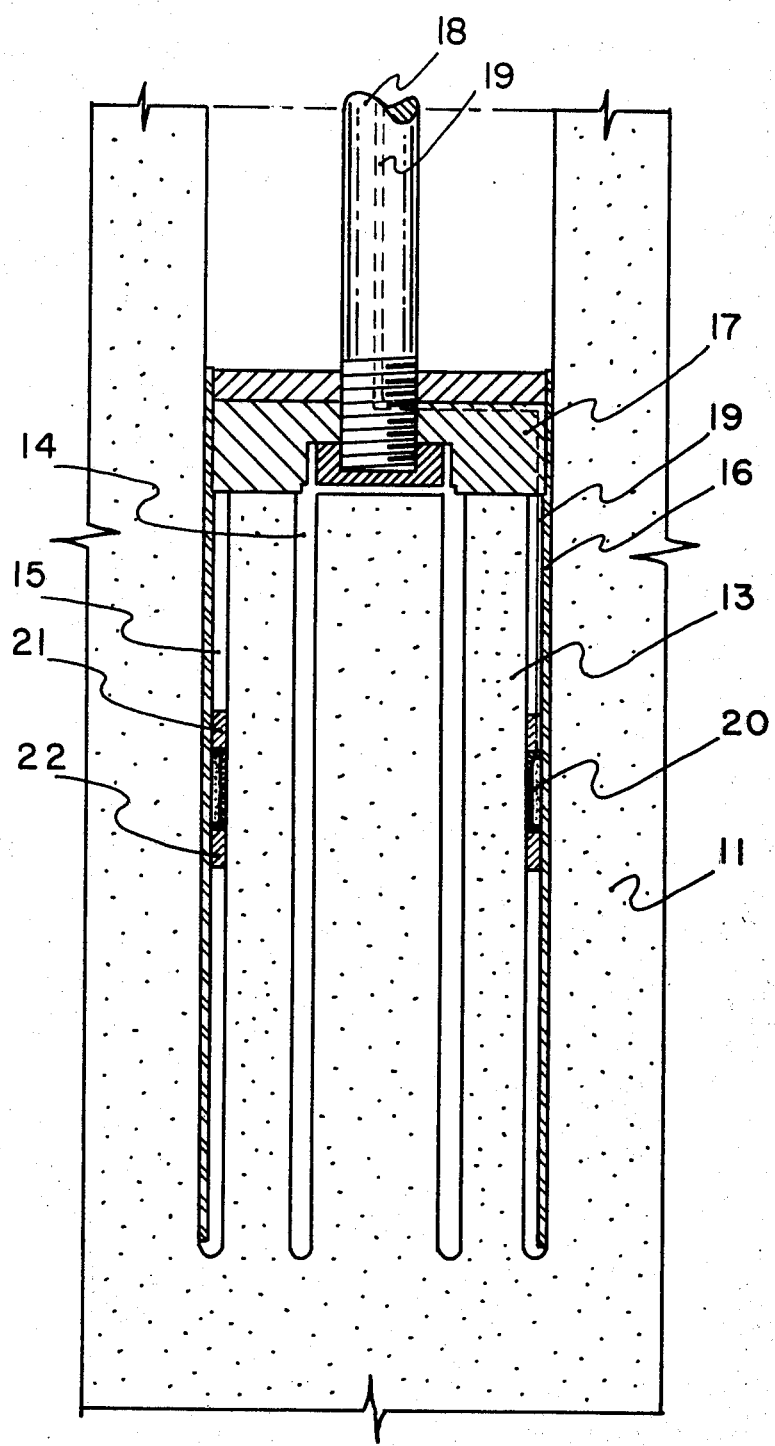
FIG. 5 is a partial sectional view of a means for (*a*) applying end pressure to the hollow cylinder of rock of FIG. 1, and (b) applying a pressure ring to the exterior of the hollow cylinder of rock of FIG. 1.

The second section of the present process, viz. that concerning the measurement of the compression strength of a rock formation, will be readily understood and easily accomplished by those of skill in the art in the light of, and with reference to the drawings and above discussion concerning the closely related measurement of tensile strength. That is to say, the very same principles, detail of operation, and spirit appertain unless otherwise particularly provided. With particular reference to FIG. 5, the measurement of compression strength of the rock formation is accomplished by:

a. cutting a second pair of concentric annular cavities 14 and 15 in the rock formation 11 to form a second hollow cylinder of rock 13 which remains connected to the rock formation at one end and is supported thereby:

b. inserting into the outer 15 of the second pair of concentric annular cavities a hollow cylindrical support 16 having an expandable collar 20, most advantageously a narrow one, secured to its inner surface and positioned perpendicularly to its longitudinal axis, the expandable collar communicating with means 19 for the supply thereto of a fluid under pressure; (it is to be noted that the cylindrical support must be hollow, as it must surround the second hollow cylinder of rock, enabling the expandable collar to exert a force against the exterior of the second hollow cylinder of rock, the force having the major moment thereof directed perpendicularly inwardly);

c. applying end pressure to the second hollow cylinder of rock by 17 through 18 and pressurizing the expandable collar 20 with fluid so that the collar expands against the second hollow cylinder of rock 13 which it surrounds and causes the second hollow cylinder of rock to fracture; and d. monitoring the fluid pressure as the expandable collar 20 is pressurized and the second hollow cylinder of rock 13 is caused to fracture, and recording the highest value of the pressure as a measure of the compression strength of the rock. Note that barrier rings 21 and 22 give direction to the expansion of expandable collar 20.

Although the present invention has been described in detail with respect to certain preferred embodiments thereof, it is apparent to those of skill in the art that variations and modifications in this detail may be accomplished without any departure from the spirt and scope of the present invention, as defined in the hereto-appended claims.

What is claimed is:

1. A process for measuring the strength of a rock formation in situ, which process comprises:
    a. cutting two concentric annular cavities in the rock formation to form a hollow cylinder of rock which remains connected to the rock formation at one end and is supported thereby;
    b. inserting into the inner annular cavity a cylindrical support having an expandable collar secured to its outer surface and positioned perpendicularly to its longitudinal axis, the expandable collar communicating with means for the supply thereto of a fluid under pressure;
    c. applying end pressure to the hollow cylinder of rock and pressurizing the expandable collar with fluid so the collar expands against the hollow cylinder of rock surrounding it and causes the hollow cylinder of rock to fracture; and
    d. monitoring the fluid pressure as the collar is pressurized and the hollow cylinder of rock is caused to fracture, and recording the highest value of the pressure as a measure of the tensile strength of the rock.

2. A process for measuring the strength of a rock formation in situ, which process comprises:
    a. cutting two concentric annular cavities in the rock formation to form a hollow cylinder of rock which remains connected to the rock formation at one end and is supported thereby;
    b. inserting into the outer annular cavity a hollow cylindrical support having an expandable collar secured to its inner surface and positioned perpendicularly to its longitudinal axis, the expandable collar communicating with means for the supply thereto of a fluid under pressure;
    c. applying end pressure to the hollow cylinder of rock and pressurizing the expandable collar with fluid so that the collar expands against the hollow cylinder of rock which it surrounds and causes the hollow cylinder of rock to fracture; and
    d. monitoring the fluid pressure as the expandable collar is pressurized and the hollow cylinder of rock is caused to fracture, and recording the highest value of the pressure as a measure of the compression strength of the rock.

3. A process for measuring the tensile strength and the compression strength of a rock formation in situ, which process comprises:
    a. cutting two concentric annular cavities in the rock formation to form a hollow cylinder of rock whick remains connected to the rock formation at one end and is supported thereby;
    b. inserting into the inner annular cavity a cylindrical support having an expandable collar secured to its outer surface and positioned perpendicularly to its longitudinal axis, the expandable collar communicating with means for the supply thereto of a fluid under pressure;
    c. applying end pressure to the hollow cylinder of rock and pressurizing the expandable collar with fluid so that the collar expands against the hollow cylinder of rock surrounding it and causes the hollow cylinder of rock to fracture;
    d. monitoring the fluid pressure as the collar is pressurized and the hollow cylinder of rock is caused to fracture, and recording the highest value of the pressure as a measure of the tensile strength of the rock;
    e. cutting a second pair of concentric annular cavities in the rock formation so that a second hollow cylinder of rock supported at one end is formed therein;
    f. inserting into the outer of the second pair of concentric annular cavities a hollow cylindrical support having an expandable collar secured to its inner surface and positioned perpendicularly to its longitudinal axis, the expandable collar communicating with means for the supply thereto of a fluid under pressure;
    g. applying end pressure to the second hollow cylinder of rock and pressurizing the expandable collar with fluid so that the collar expands against the second hollow cylinder of rock which it surrounds and causes the second hollow cylinder of rock to fracture; and
    h. monitoring the fluid pressure as the expandable collar is pressurized and the second hollow cylinder of rock is caused to fracture, and recording the highest value of the pressure as a measure of the compression strength of the rock.

4. The process of claim 3, wherein the rock formation to be tested is an underground rock formation, and the hollow cylinders of rock are cut in the formation at the base of a bore hole.

5. The process of claim 3, wherein an inflatable membrane is employed as an expandable collar of a cylindrical support.

* * * * *